United States Patent
Okada et al.

(10) Patent No.: US 8,211,674 B2
(45) Date of Patent: Jul. 3, 2012

(54) METHOD OF MAKING THEANINE

(75) Inventors: Yukitaka Okada, Yokkaichi (JP);
Makoto Ozeki, Yokkaichi (JP);
Nobuyuki Aoi, Yokkaichi (JP)

(73) Assignee: Taiyokagaku Co., Ltd., Yokkaichi-Shi (JP)

( * ) Notice: Subject to any disclaimer, the term of this patent is extended or adjusted under 35 U.S.C. 154(b) by 213 days.

(21) Appl. No.: 11/571,074

(22) PCT Filed: Jun. 22, 2005

(86) PCT No.: PCT/JP2005/011420
§ 371 (c)(1),
(2), (4) Date: Dec. 21, 2006

(87) PCT Pub. No.: WO2006/001296
PCT Pub. Date: Jan. 5, 2006

(65) Prior Publication Data
US 2007/0224667 A1    Sep. 27, 2007

(30) Foreign Application Priority Data

Jun. 28, 2004 (JP) .................... 2004-189048
Dec. 27, 2004 (JP) .................... 2004-376443

(51) Int. Cl.
*C12P 13/14* (2006.01)
(52) U.S. Cl. .......... 435/110; 435/41; 435/128; 435/132; 435/155
(58) Field of Classification Search .......... None
See application file for complete search history.

(56) References Cited

U.S. PATENT DOCUMENTS

| 6,190,879 | B1 * | 2/2001 | Bech et al. ............... 435/68.1 |
| 7,273,621 | B2 * | 9/2007 | Ozeki et al. ............... 424/451 |
| 2006/0105437 | A1 | 5/2006 | Tachiki et al. | |

FOREIGN PATENT DOCUMENTS

| JP | 05-068578 A1 | 3/1993 |
| JP | 05-328986 A1 | 12/1993 |
| JP | 08-089266 A1 | 4/1996 |
| JP | 11-225789 A1 | 8/1999 |
| WO | WO 2004/016798 A1 | 2/2004 |

OTHER PUBLICATIONS

Tachiki et al., Biosci. Biotechnol. Biochem. 1998, vol. 62, No. 7, p. 1279-1283.*
Koibuchi et al., Applied Microbiol. Biotechnol. 2000, vol. 54, p. 59-68.*
Cook et al., Journal of Bacteriology, 1981, vol. 148, No. 1, p. 365-367.*
Suzuki et al., Enzyme and Microbial Technology, 2002, vol. 31, p. 884-889.*
Minami et al., Enzyme and Microbial Technology, Mar. 2003, vol. 32, p. 431-438.*
Nandakumar et al., Journal of Molecular Catalysis B: Enzymatic 23, 2003, vol. 23, p. 87-100.*
Cook et al. , Journal of Bacteriology, 1981, vol. 148, No. 1, p. 365-367.*
Hwang et al., Agric. Biol. Chem., 1985, vol. 49, No. 11, p. 3255-3264.*

* cited by examiner

*Primary Examiner* — Kade Ariani
(74) *Attorney, Agent, or Firm* — Burr & Brown (57) ABSTRACT

In a method of making theanine, glutaminase is derived from microbes of one or more of *Bacillus*, mold and yeast is caused to act on glutamine and ethylamine derivative.

6 Claims, 4 Drawing Sheets

FIGURE 1

| TYPES OF MICROBES | | EMBODIMENT1<br>Bacillus subtilis | EMBODIMENT2<br>Bacillus amyloliquefaciens | EMBODIMENT3<br>Bacillus coagulans | EMBODIMENT4<br>Bacillus licheniformis | EMBODIMENT5<br>Bacillus cereus | COMPARED EXAMPLE1<br>Pseudomonas nitroreducens |
|---|---|---|---|---|---|---|---|
| GLUTAMINASE SPECIFIC ACTIVITY OF CULTURE SUPERNATANT (mU/mg) | | 67 | 53 | 43 | 40 | 5 | 15 |
| MOL CONVERSION RATIO FROM L-GLUTAMINE (%) | THEANINE | 75 | 74 | 70 | 69 | 55 | 50 |
| | GLUTAMIC ACID | 2 | 3 | 5 | 7 | 10 | 10 |

FIGURE 2

| TYPES OF MICROBES | | EMBODIMENT8 Aspergillus oryzae | EMBODIMENT9 Aspergillus niger | EMBODIMENT10 Rizopus stolonifer | EMBODIMENT11 Mucor sponosus | COMPARED EXAMPLE1 Pseudomonas nitroreducens |
|---|---|---|---|---|---|---|
| GLUTAMINASE SPECIFIC ACTIVITY OF CULTURE SUPERNATANT (mU/mg) | | 42 | 39 | 15 | 5 | 15 |
| MOL CONVERSION RATIO FROM L-GLUTAMINE (%) | THEANINE | 72 | 73 | 65 | 52 | 50 |
| | GLUTAMIC ACID | 5 | 4 | 5 | 9 | 10 |

FIGURE 3

| TYPES OF MICROBES | | EMBODIMENT12 Saccharomyces cerevisiae | EMBODIMENT13 Saccharomyces rouxii | EMBODIMENT14 Candida utilis | EMBODIMENT15 Candida antarctica | EMBODIMENT16 Honsenulla anomala | COMPARED EXAMPLE1 Pseudomonas nitroreducens |
|---|---|---|---|---|---|---|---|
| GLUTAMINASE SPECIFIC ACTIVITY OF CULTURE SUPERNATANT (mU/mg) | | 45 | 40 | 30 | 25 | 15 | 15 |
| MOL CONVERSION RATIO FROM L-GLUTAMINE (%) | THEANINE | 75 | 70 | 71 | 72 | 54 | 50 |
| | GLUTAMIC ACID | 4 | 5 | 6 | 5 | 11 | 10 |

FIGURE 4

METHOD OF MAKING THEANINE

BACKGROUND OF THE INVENTION

1. Field of the Invention

The present invention relates to a novel method of making theanine.

2. Description of the Related Art

Theanine is known as a principal component of deliciousness of green tea and is an important substance as a flavor component of food such as tea. It is pointed out that γ-glutamyl derivative containing theanine acts as a biologically active substance in animals and plants. For example, it is reported that theanine or L-glutamine competes for convulsion caused by caffeine (Chem. Pharm. Bull. 19 (7) 1301-1307 (1971)). Thus, these compounds are considered to act on the central nervous system and expected to be useful as a biologically active substance.

Conventionally, theanine is generally extracted from dried tea leaves obtained in tea plantations where refined green tea containing theanine is produced. However, this method has two defects, namely, (1) only about 1.5% theanine is stored per predetermined amount of dried tea leaves and (2) photosynthesis is actively carried out in ordinary tea plantations and accordingly, synthesized theanine is quickly resolved, whereupon an amount of stored theanine is small. Thus, it is difficult and not practical to produce a sufficient amount of theanine by the extraction from the dried tea leaves.

Accordingly, new industrial production methods of theanine have been proposed. As one of the methods, a chemical organic synthesis of theanine has been reported (Chem. Pharm. Bull. 19 (7) 1301-1307 (1971)). However, the organic synthesis reaction has a low yield and requires a complicated operation in separation and refinement of composition and the like. Furthermore, an enzyme method has been reported as another industrial production method. In this enzyme method, theanine is synthesized from L-glutamine and ethylamine through the use of γ-glutamyl radical group transition reaction of glutaminase derived from *Pseudomonas* (JP-A-H11-225789). Additionally, another enzyme method has been developed in which this enzyme is fixed to a carrier (JP-A-H05-328986). However, when glutaminase derived from *Pseudomonas* is used, L-glutamic acid is synthesized as side reaction product by hydrolysis reaction as well as theanine. Accordingly, L-glutamic acid as a by-product complicates refinement of theanine.

SUMMARY OF THE INVENTION

Therefore, an object of the present invention is to provide an efficient method of making theanine.

The inventors made research to overcome the above-described problem and found that theanine was able to be synthesized at high yield through the use of glutaminase derived from microbes of one or more of *Bacillus*, mold and yeast, and an amount of by-product was exceedingly small. Thus, the inventors completed the invention. More specifically, the present invention is directed to a method of making theanine wherein glutaminase derived from microbes of one or more of *Bacillus*, mold and yeast is caused to act on glutamine and ethylamine derivative.

The invention provides an efficient novel method of making theanine and can realize simple industrially advantageous production. More specifically, a higher conversion rate to theanine was admitted through the use of glutaminase derived from microbes of one or more of *Bacillus*, mold and yeast, whereupon industrial production is realized.

BRIEF DESCRIPTION OF THE DRAWINGS

Other objects, features and advantages of the present invention will become clear upon reviewing the following description of the embodiments with reference to the accompanying drawings, in which.

DETAILED DESCRIPTION OF THE INVENTION

Embodiments of the present invention will be described in detail. However, the technical scope of the invention should not be limited by the following description of embodiments but can be practiced in various modified forms. Furthermore, it is noted that the technical scope of the invention should encompass the scope of equivalence.

Theanine used in the invention is a glutamic acid derivative contained in tea leaves and a principal component of deliciousness of tea. Theanine is used as a food additive for use as gustatory. More specifically, theanine is a compound such as γ-glutamilethylamide or L-glutamic acid-γ-ethylamide.

The ethylamine derivative used in the invention is ethylamine, ethylamine hydrochloride, ethylamine chloroaurate, ethylamine fatty acid salt, ethylamine picrate, N-benzenesulfonyl compound of ethylamine, N-p-toluenesulfonyl compound of ethylamine and the like. There is no specific limitation to them. Furthermore, ethylamine and ethylamine hydrochloride are particularly preferred.

Glutaminase used in the invention has glutaminase activity hydrolyzing L-glutamine thereby to produce L-glutamic acid and is used to improve taste of fermentative food such as Japanese "miso" and soy sauce. It is known that γ-glutamil transition activity is higher than hydrolytic activity in glutaminase under alkaline conditions. Glutaminase can also be used for synthesis of alkylamide such as theanine.

Glutaminase activity in the invention is measured by causing enzyme to react with L-glutamine serving as a substrate to determine L-glutamic acid produced. An amount of produced L-glutamic acid can be measured using a commercially available kit, for example, F kit L-glutamic acid (Roche Diagnostics). As the unit for the present enzyme, an amount of enzyme producing 1 μmol glutamic acid per min. is defined as "mU". Using this definition, an amount of enzyme per mg protein in a solution is defined as glutaminase activity mU/mg.

*Bacillus* used in the invention is cytomorphologically a bacteria having the characteristics of gram positive aerobic bacteria, *bacillus*, sporulatability, movability and the like.

There is no specific limitation to glutaminase derived from *Bacillus* in the invention. However, such glutaminase is preferably enzyme derived from *Bacillus subtilis, Bacillus amyloliquefaciens, Bacillus coagulans, Bacillus lentus, Bacillus licheniformis, Bacillus polymixa, Bacillus stearothermophilus* or *Bacillus thermoproteolyticus*. From the viewpoint that bacteria with high glutaminase specific activity is preferred, glutaminase derived from *Bacillus subtilis* or *Bacillus amyloliquefaciens* is most preferred.

Glutaminase derived from *Bacillus* may be produced from modified bacteria such as gene recombination by application of biotechnology.

Mold in the invention is a general term for an indefinite aggregate with entangled mold hyphae in fungus and can be found in Phycomycetes, many of Ascomycetes and part of Basidiomycetes.

There is no specific limitation to glutaminase derived from mold in the invention. However, such glutaminase is preferably enzyme derived from *Aspergillus oryzae, Aspergillus niger, Penicillium notatum, Rhizopus stolonifer* or *Mucor sponosus*. From the viewpoint that bacteria with high glutaminase specific activity is preferred, glutaminase derived from *Aspergillus oryzae* or *Aspergillus niger* is most preferred.

Furthermore, glutaminase derived from mold may be produced from modified bacteria such as gene recombination by application of biotechnology.

Yeast in the invention is a fungus belonging to Ascomycetes. The yeast contains no chlorophyll and breeds by gemmation and sometimes by division. The yeast is used for production of alcoholic beverages, soy sauce, bread and the like.

There is no specific limitation to glutaminase derived from yeast in the invention. However, such glutaminase is preferably enzyme derived from *Saccharomyces cerevisiae, Saccharomyces rouxii, Candida utilis, Candida antarctica, Hansenulla anomala, Schizosaccharomyces octosporus*. From the viewpoint that bacteria with high glutaminase specific activity is preferred, glutaminase derived from *Saccharomyces cerevisiae, Saccharomyces rouxii, Candida utilis* or *Candida antarctica* is most preferred.

Furthermore, glutaminase derived from yeast may be produced from modified bacteria such as gene recombination by application of biotechnology.

The aforesaid glutaminase derived from microbes of one or more of *Bacillus*, mold and yeast may be (1) microbes or (2) crude enzyme extracted from microbes. However, from the viewpoint of a theanine conversion ratio, it is preferable to refine glutaminase from microbes. Any conventional enzyme refining method may be employed for refinement of glutaminase. For example, column chromatography, partition with use of a solvent, dialysis, ultrafiltration, electrophoresis, fractional salting out by the use of normal salt, fractional precipitation by the use of alcohol or acetone, high performance liquid chromatography (HPLC) and the like can be exemplified. Of these, it is preferable to refine glutaminase by the combination of partition with use of a solvent, various types of chromatography and HPLC. Furthermore, glutaminase may be refined by combining one or more of glutaminase may be refined by the combination of CM-cellulose column chromatography, sephadex G150 column chromatography, hydroxyapatite column chromatography, butyl-Toyopearl® column chromatography.

Thus, in the method of making theanine according to the invention, glutaminase is derived from one or more of *Bacillus, Penicillium, Rizopus, Mucor, Aspergillus, Hansenulla, Schizosaccaromyces* and *Candida*. It is preferable to cause the glutaminase to act on glutamine and ethylamine derivative. In this case, (1) it is preferable that the microbes be cultured under the condition where culture supernatant of the microbes has a specific activity of not less than 10 mU/mg. Furthermore, (2) it is preferable that the glutaminase have a ratio (theanine/glutamic acid) of theanine as a main product to a glutamic acid as a by-product larger than 5, form the viewpoint of reducing by-product.

There is no specific limitation to fluidity in the synthesis of theanine enzyme in the invention. However, it is preferable that pH range from about 9 to 12. It is more preferable that pH range from about 10 to 11. Furthermore, there is no specific limitation to a reaction temperature. However, it is preferable that the reaction temperature range from about 0° C. to 45° C. It is more preferable that the reaction temperature range from about 4° C. to 30° C. There is no specific limitation to the densities of L-glutamine and ethylamine derivative. However, it is preferable that the density of L-glutamine be not less than about 0.1 mol and the density of ethylamine derivative be not less than about 1 mol.

L-glutamine in the invention includes pure L-glutamine and may contain suitable organic or inorganic salt, such as L-glutamine sodium salt.

Any known amino acid refining method may be used in order that theanine synthesized by the method of the invention may be isolated from reaction liquid and refined. For example, column chromatography, partition with use of a solvent, dialysis, crystallization, ultrafiltration, electrophoresis, fractional salting out by the use of normal salt, fractional precipitation by the use of alcohol or acetone, high performance liquid chromatography (HPLC) and the like can be exemplified. Of these, it is preferable to refine glutaminase by the combination of partition with use of a solvent, various types of chromatography and HPLC. Furthermore, glutaminase may be refined by combining one or more of glutaminase may be refined by the combination of CM-cellulose column chromatography, sephadex G150 column chromatography, hydroxyapatite column chromatography, butyl-Toyopearl column chromatography.

The carrier in the invention fixes glutaminase. For example, the carrier may be an inorganic carrier such as Celite, silious earth, kaolinite, silica gel, molecular sieves, porous glass, activated charcoal, calcium carbonate, ceramics or the like or an organic high polymer such as ceramic powder, polyvinyl alcohol, polypropylene, chitosan, ion-exchange resin, chelate resin, synthetic adsorptive resin or the like. However, there is no specific limitation to the carrier in the invention.

The invention will be described in more detail by way of embodiments and test examples. These embodiments and test examples constitute a part of the embodiments of the invention but the invention should not be limited to the embodiments and test examples.

Embodiment 1:

*Bacillus subtilis* was cultured at 30° C. in a culture medium of pH 7.0 containing 0.3% glucose, 3.0% polypeptone, 1.0% yeast extract and 0.5% sodium chloride. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA; Amersham Bioscience KK), whereby refined glutaminase was obtained. Glutaminase specific activity of the culture supernatant was 67 mU/mg.

Embodiment 2:

*Bacillus amyloliquefaciens* was cultured at 30° C. in a culture medium of pH 7.0 containing 0.3% glucose, 3.0% polypeptone, 1.0% yeast extract and 0.5% sodium chloride. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA, Amersham Bioscience KK), whereby refined glutaminase was obtained. Glutaminase specific activity of the culture supernatant was 53 mU/mg.

Embodiment 3:

*Bacillus coagulans* was cultured at 30° C. in a culture medium of pH 7.0 containing 0.3% glucose, 3.0% polypeptone, 1.0% yeast extract and 0.5% sodium chloride. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA, Amersham Bioscience KK), whereby refined glutaminase was obtained. Glutaminase specific activity of the culture supernatant was 43 mU/mg.

Embodiment 4:

*Bacillus licheniformis* was cultured at 30° C. in a culture medium of pH 7.0 containing 0.3% glucose, 3.0% polypeptone, 1.0% yeast extract and 0.5% sodium chloride. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA; Amersham Bioscience KK), whereby refined glutaminase was obtained. Glutaminase specific activity of the culture supernatant was 40 mU/mg.

Embodiment 5:

*Bacillus cereus* was cultured at 30° C. in a culture medium of pH 7.0 containing 0.3% glucose, 3.0% polypeptone, 1.0% yeast extract and 0.5% sodium chloride. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desali-nated using a UF film (UFP-5-C-3MA, Amersham Bioscience KK), whereby refined glutaminase was obtained. Glutaminase specific activity of the culture supernatant was 5 mU/mg.

COMPARED EXAMPLE 1

Preparation of Refined Glutaminase Derived from *Pseudomonas nitroreducens*

*Pseudomonas nitroreducens* was cultured in a 30 L jar fermenter (30 lit., ventilation 1 vvm=25 L/min., revolution 2000 rpm) for about 20 hours using a culture fluid (pH 7) containing 0.6% sodium glutamate, 0.1% yeast extract, 1.0% glucose, 0.05% $KH_2PO_4$, 0.05% $K_2HPO_4$, 0.07% $MgSO_4$, $7H_2O$ and 0.01% EDTA-Fe. After having been washed, bacterial cells in the obtained culture fluid were suspended in 7.5 L of 30 mM buffer solution of potassium phosphate (pH 7.0) and ultrasonically crushed in a temperature range from 5° C. to 20° C., where upon crushed bacterial cells were obtained.

The crushed bacterial cells were fractionated using ammonium sulfate while pH was adjusted to 7 by 7% ammonia water, whereby 45 to 90% saturation fraction was obtained. The obtained saturation fraction was dissolved into a buffer solution of 0.01 M potassium phosphate to be dialyzed. A dialysate was adsorbed using DEAE-cellulose column (15× 60 cm) and glutaminase was eluted by a buffer solution containing 0.1 M salt, whereby glutaminase solution was obtained. The obtained glutaminase solution was condensed and desalinated using a UF film (UFP-5-C-3MA, Amersham Bioscience KK), whereby refined glutaminase was obtained. Glutaminase specific activity of the culture supernatant was 15 mU/mg.

EXAMPLE 6

Theanine Enzyme Synthesis by Refined Glutaminase

Using refined glutaminase (0.1 mL), theanine enzyme synthesis was carried out for 10 mL substrate solution (0.5 M L-glutamine and various densities of ethylamine) under the condition where pH was 10.0 and the temperature was 30° C.

Embodiment 7: Determination of Amount of Theanine and Glutamic Acid

An enzyme reaction liquid in which theanine enzyme synthesis was executed was diluted suitably and thereafter, HPLC was carried out for the diluted reaction liquid so that amounts of theanine and glutamic acid were determined. A mol conversion ratio from an amount of glutamine (mol/L) of the substrate was calculated using obtained amounts of theanine and glutamic acid (mol/L). TABLE 1 shows the conditions for determination by HPLC.

TABLE 1

| | |
|---|---|
| Analysis column: | Develosil ODS HG-5/Nomura Chemical Co., Ltd. |
| Detector: | Waters2487 Dual λ UV/VIS Detector/Waters |
| Sample of theanine: | L-theanine/Kurita Industry Co., Ltd. |
| Inner standard substance: | Nicotinoamide/NACALAI TESQUE, INC. |
| Mobile phase: | Pure water:methanol:trifluoroacetic acid = 980:20:1 |

TEST EXAMPLE 1

Theanine Enzyme Synthesis by Glutaminase Derived from *Bacillus* and Glutaminase Derived from *Pseudomonas*

Figure 1:
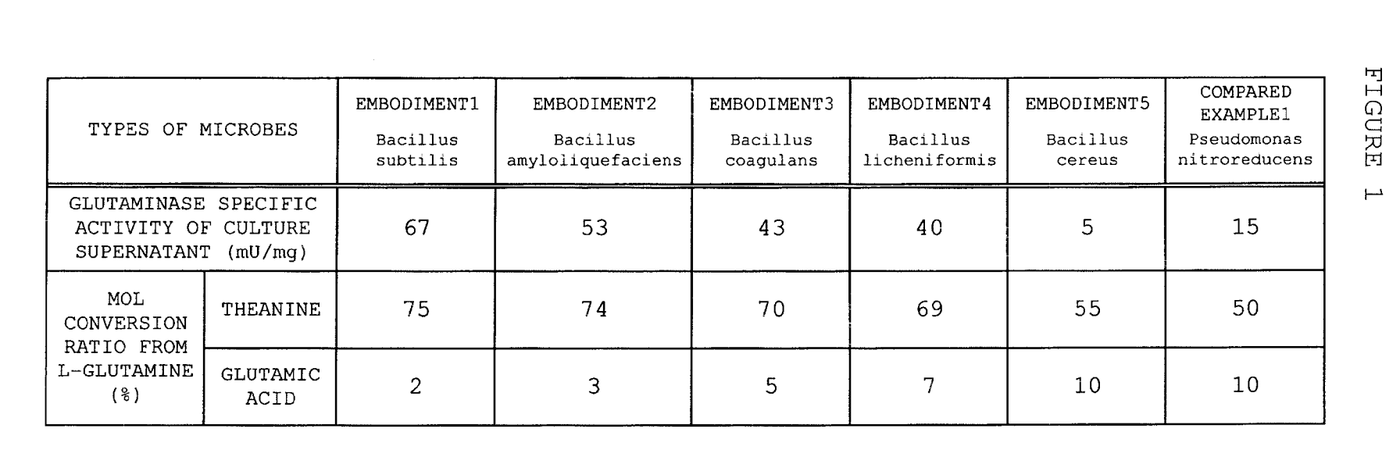
FIG. 1 shows an amount of synthesized theanine and an amount of glutamic acid in the case where enzymatic synthesis of theanine from L-glutamine and ethylamine is carried out through the use of glutaminase derived from *Bacillus* and glutaminase derived from *Pseudomonas*.

A theanine enzyme synthesis test was carried out under the conditions of embodiment 6 using glutaminase derived from each microorganism prepared in embodiments 1 to 5 and compared example 1. Amounts of theanine and glutamic acid after the test were measured under the conditions of embodiment 7. FIG. 1 shows the results of the test.

A mol conversion ratio from L-theanine to theanine is not less than 50% when glutaminase of each of embodiments 1 to 5 and compared example 1 is used. In particular, the mol conversion ratios of glutaminase of embodiments 1 to 4 reach high values of 78%, 76%, 72% and 70% respectively. On the other hand, regarding mol conversion ratios from L-glutamine to L-glutamic acid (production of by-product), glutaminase of each of embodiment 5 and compared example 1 has a high value of not less than 15% although glutaminase of each of embodiments 1 to 4 has a low value of not more than 6%. When theanine is synthesized using glutaminase, it is preferable that a mol conversion ratio to L-glutamic acid (by-product) be low as well as that a mol conversion ratio to theanine be high. As a result, the process of refining theanine can be simplified. In order that the aforesaid conditions may be met, it is preferable to use glutaminse derived from *Bacillus* and having a glutaminse specific activity of culture supernatant thereof not less than 10 mU/mg.

Embodiment 8:

*Aspergilus oryzae* was cultured at 30° C. in a culture medium of pH 5.0 containing 2.0% malt extract, 2.0% glucose, 0.1% peptone and 0.1% yeast extract. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA, Amersham Bioscience KK), whereby refined glutaminase was obtained. Glutaminase specific activity of the culture supernatant was 42 mU/mg.

Embodiment 9:

*Aspergilus niger* was cultured at 30° C. in a culture medium of pH 5.0 containing 2.0% malt extract, 2.0% glucose, 0.1% peptone and 0.1% yeast extract. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA, Amersham Bioscience KK), whereby refined glutaminase was obtained. Glutaminase specific activity of the culture supernatant was 39 mU/mg.

Embodiment 10:

*Rhizopus stolnifer* was cultured at 30° C. in a culture medium of pH 5.0 containing 2.0% malt extract, 2.0% glucose, 0.1% peptone and 0.1% yeast extract. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA, Amersham Bioscience KK), whereby refined glutaminase was obtained. Glutaminase specific activity of the culture supernatant was 15 mu/mg.

Embodiment 11:

*Mucor sponosus* was cultured at 30° C. in a culture medium of pH 5.0 containing 2.0% malt extract, 2.0% glucose, 0.1% peptone and 0.1% yeast extract. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA, Amersham Bioscience KK), whereby refined glutaminase was obtained. Glutaminase specific activity of the culture supernatant was 5 mu/mg.

TEST EXAMPLE 2

Theanine Enzyme Synthesis by Glutaminase Derived from Mold and Glutaminase Derived from *Pseudomonas*

Figure 2:
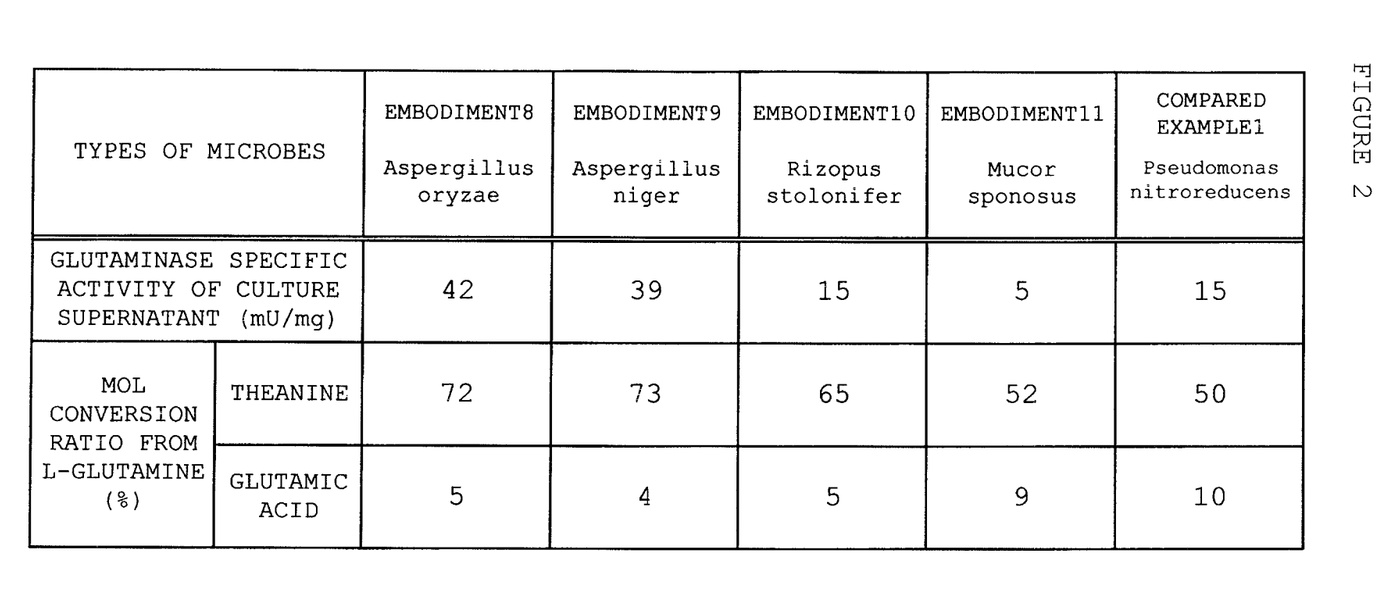
FIG. 2 shows an amount of synthesized theanine and an amount of glutamic acid in the case where enzymatic synthesis of theanine from L-glutamine and ethylamine is carried out through the use of glutaminase derived from mold and glutaminase derived from *Pseudomonas*.

A theanine enzyme synthesis test was carried out under the conditions of embodiment 6 using glutaminase derived from each microorganism prepared in embodiments 8 to 11 and compared example 1. Amounts of theanine and glutamic acid after the test were measured under the conditions of embodiment 7. FIG. 2 shows the results of the test.

A mol conversion ratio from L-theanine to theanine is not less than 50% when glutaminase of each of embodiments 8 to 11 and compared example 1 is used. In particular, the mol conversion ratios of glutaminase of embodiments 8 and 9 reach high values of 72% and 73% respectively. On the other hand, regarding mol conversion ratios from L-glutamine to L-glutamic acid (production of by-product), glutaminase of compared example 1 has a high value of not less than 10% although glutaminase of each of embodiments 8 and 9 has a low value of not more than 5%. When theanine is synthesized using glutaminase, it is preferable that a mol conversion ratio to L-glutamic acid (by-product) be low as well as that a mol conversion ratio to theanine be high. As a result, the process of refining theanine can be simplified. In order that the aforesaid conditions may be met, it is preferable (1) that glutaminase is derived from mold (particularly, *Asppergillus*, *Rozopus* and *Mucor*) and has a specific activity of not less than 10 mU/mg or (2) that the glutaminase has a ratio (a ratio of theanine/glutamic acid=X) of theanine as a main product to a glutamic acid as a by-product represented as X>5 in a mol conversion ratio from L-glutamine.

Embodiment 12:

*Saccharomyces cerevisiae* was cultured at 30° C. in a culture medium of pH 5.0 containing 0.3% malt extract, 0.3% yeast extract, 0.5% peptone and 1.0% glucose. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UE film (UFP-5-C-3MA, Amersham Bioscience KK), whereby refined glutaminase was obtained. Glutaminase specific activity of the culture supernatant was 45 mU/mg.

Embodiment 13:

Saccharomyces rouxii was cultured at 30° C. in a culture medium of pH 5.0 containing 0.3% malt extract, 0.3% yeast extract, 0.5% peptone and 1.0% glucose. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA, Amersham Bioscience KK), whereby refined glutaminase was obtained. Glutaminase specific activity of the culture supernatant was 40 mU/mg.

Embodiment 14:

Candida utilis was cultured at 30° C. in a culture medium of pH 5.0 containing 0.3% malt extract, 0.3% yeast extract, 0.5% peptone and 1.0% glucose. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA; Amersham Bioscience KK), whereby refined glutaminase was obtained. Glutaminase specific activity of the culture supernatant was 30 mU/mg.

Embodiment 15:

Candida antarctica was cultured at 30° C. in a culture medium of pH 5.0 containing 0.3% malt extract, 0.3% yeast extract, 0.5% peptone and 1.0% glucose. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA, Amersham Bioscience KK), whereby refined glutaminase was obtained. Glutaminase specific activity of the culture supernatant was 25 mU/mg.

Embodiment 16:

Hansenulla anomala was cultured at 30° C. in a culture medium of pH 5.0 containing 0.3% malt extract, 0.3% yeast extract, 0.5% peptone and 1.0% glucose. An obtained culture fluid was processed by a centrifugal separator, whereupon culture supernatant was obtained. Cold ethanol was added to the culture supernatant, and obtained precipitation was processed by a centrifugal separator and then recovered. Obtained precipitate was dissolved into a buffer solution of phosphoric acid (pH 7.0) and then dialyzed. A dialysate was adsorbed using DEAE-Sepharose Fast Flow and thereafter, the purity of protein was improved by elution by salt solution. Obtained glutaminase solution was condensed and desalinated using a UF film (UFP-5-C-3MA, Amersham Bioscience KK), whereby refined glutaminase was obtained. Glutaminase specific activity of the culture supernatant was 15 mU/mg.

TEST EXAMPLE 3

Theanine Enzyme Synthesis by Glutaminase Derived from Yeast and Glutaminase Derived from *Pseudomonas*

Figure 3:
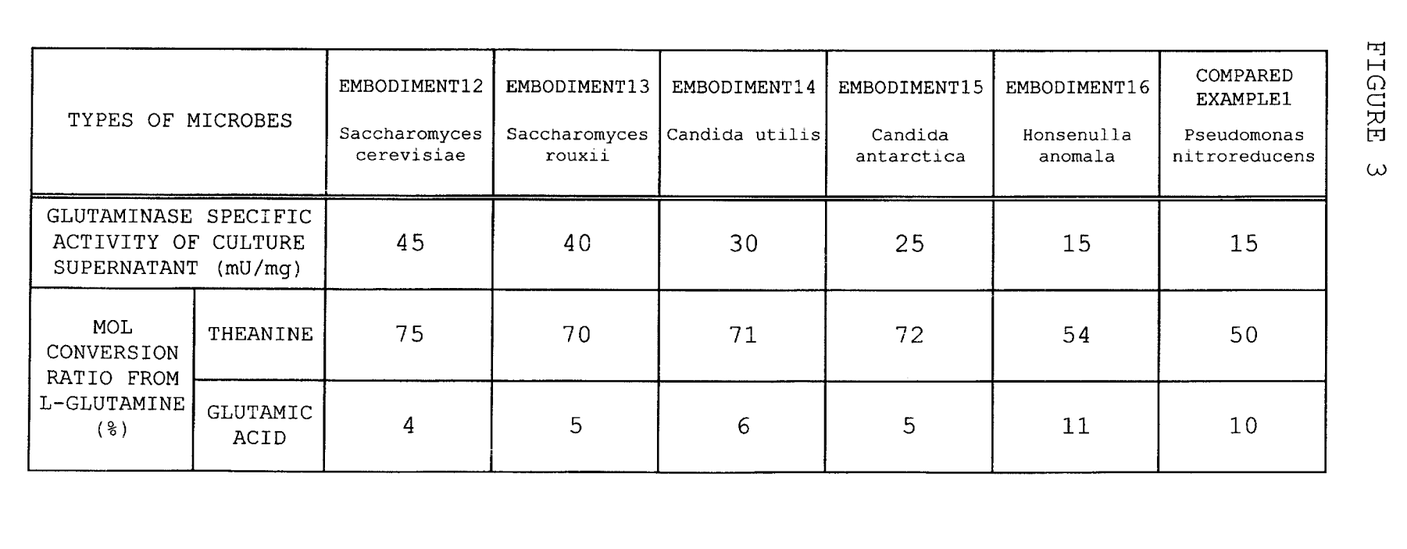
FIG. 3 shows an amount of synthesized theanine and an amount of glutamic acid in the case where enzymatic synthesis of theanine from L-glutamine and ethylamine is carried out through the use of glutaminase derived from yeast and glutaminase derived from *Pseudomonas*.

A theanine enzyme synthesis test was carried out under the conditions of embodiment 6 using glutaminase derived from each microorganism prepared in embodiments 12 to 16 and compared example 1. Amounts of theanine and glutamic acid after the test were measured under the conditions of embodiment 7. FIG. 3 shows the results of the test.

A mol conversion ratio from L-theanine to theanine is not less than 50% when glutaminase of each of embodiments 12 to 16 and compared example 1 is used. In particular, the mol conversion ratios of glutaminase of embodiments 12 to 15 reach high values of not less than 70% respectively. On the other hand, regarding mol conversion ratios from L-glutamine to L-glutamic acid (production of by-product), glutaminase of compared example 1 has a high value of not less than 10% although glutaminase of each of embodiments 12 to 15 has a low value. When theanine is synthesized using glutaminase, it is preferable that a mol conversion ratio to L-glutamic acid (by-product) is low as well as that a mol conversion ratio to theanine be high. As a result, the process of refining theanine can be simplified. In order that the aforesaid conditions may be met, it is preferable that glutaminase is derived from yeast (particularly, *Saccharomyces* and *Candida*) and has a specific activity of not less than 10 mU/mg.

Embodiment 17: Preparation of Fixed Glutaminase Using CHITOPEARL® 4010

CHITOPEARL® 4010 (manufactured by Fuji Spinning Co., Ltd.) was immersed in a buffer solution of 50 mM sodium phosphate (pH 7.4) for 24 hours. After equilibration, 10 mL CHITOPEARL® 4010 was immersed in 25 mL glutaminase (15 mg/mL) prepared in embodiment 3 was shaken for about two hours. Thereafter, CHITOPEARL® 4010 from which adherent liquid had been removed was added to 2.5% glutaraldehyde and then shaken for two hours. After process of glutaraldehyde, CHITOPEARL® 4010 washed using a buffer solution of 50 mM sodium phosphate (pH 7.4) an amount of which is 30 times larger than an amount of CHITOPEARL® 4010. The washing was continued until absorbance (280 nm) became equal to or smaller than 0.01. CHITOPEARL® 4010 was charged into a column.

Embodiment 18: Enzyme Reaction by Fixed Glutaminase

With use of the fixed glutaminase prepared in embodiment 17, a substrate solution (4% glutamine and 25% ethylamine, pH 10.0) was passed through the column at a flow rate SV=0.2 at 30° C. As a result, theanine was able to be obtained at the yield of 70%.

Embodiment 17: Preparation of Fixed Glutaminase Using Anion Exchange Resin 10 mL DIAION®HPA25 (Mitsubishi Chemical Corporation) which is an anion exchange resin was added to 25 mL refined glutaminase (15 mg/mL) obtained in embodiment 3. Subsequently, the mixture was shaken for about two hours. Thereafter, DIAION® HPA25 from which adherent liquid had been removed was added to 2.5% glutaraldehyde solution and then shaken for further two hours. After process of glutaraldehyde, DIAION® HPA25 washed using a buffer solution of 50 mM sodium phosphate (pH 7.4) an amount of which is 30 times larger than an amount of CHITOPEARL® 4010. The washing was continued until absorbance (280 nm) became equal to or smaller than 0.01. DIAION®HPA25 was charged into a column.

Embodiment 20: Enzyme Reaction by Fixed Glutaminase

With use of the fixed glutaminase prepared in embodiment 19, a substrate solution (4% glutamine and 25% ethylamine, pH 10.0) was passed through the column at a flow rate SV=0.2 at 30° C. As a result, theanine was able to be obtained at the yield of 70%.

Embodiment: Refinement of Theanine

In isolation and refinement of theanine from reaction liquid, ethylamine was removed from the reaction liquid by vacuum concentration and thereafter, desalination was carried out using a reverse osmosis (RO) membrane. Subsequently, the reaction liquid was applied to column chromatography of Dowex 50×8 and Dowex 1×2 and then treated by ethanol.

Figure 4:
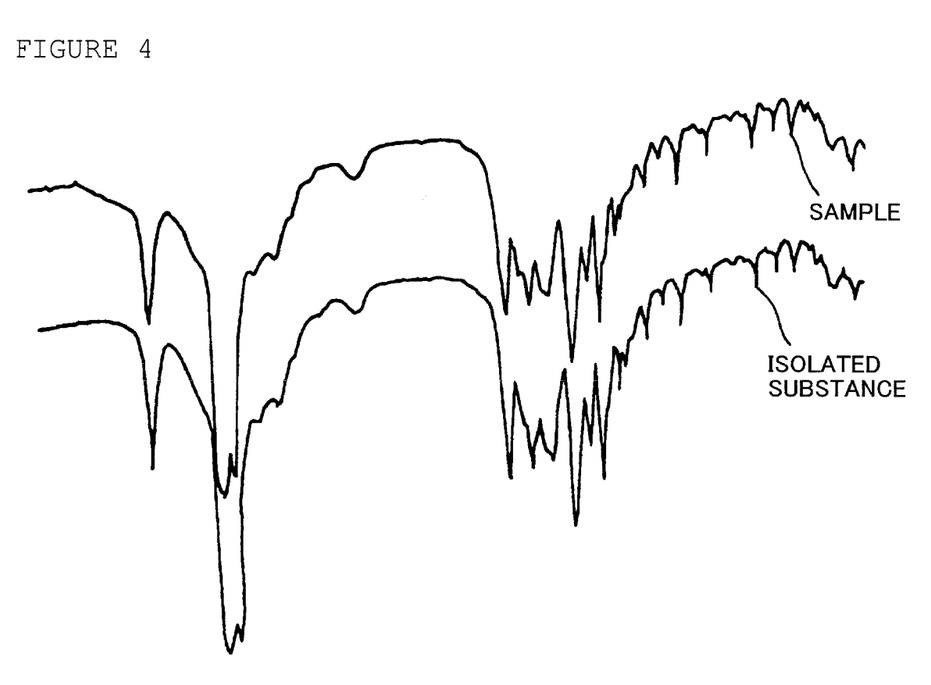
FIG. 4 is a graph showing IR spectrum of sample theanine and isolated substance.

When applied to an amino acid analyzer and a paper chromatography, the isolated substance exhibited the same behavior as a standard substance of theanine. Furthermore, hydrolysis of the isolated substance using hydrochloric acid or glutaminase yielded L-glutamine and ethylamine at a ratio of 1:1. Thus, since hydrolysis of the isolated substance by glutaminase was thus possible, ethylamine was proved to be combined with the gamma-position of L-glutamine. Furthermore, it was confirmed by L-glutamic acid dehydrogenaze (GluDH) that glutamine yielded by hydrolysis was of L-type. FIG. 4 shows infrared absorption spectrometry (IR) spectra of theanine sample and isolated substance. Both substances exhibited spectra similar to each other. Consequently, the isolated substance was proved to be theanine.

The foregoing description and drawings are merely illustrative of the principles of the present invention and are not to be construed in a limiting sense. Various changes and modifications will become apparent to those of ordinary skill in the art. All such changes and modifications are seen to fall within the scope of the invention as defined by the appended claims.

What is claimed is:

1. A method of making theanine comprising the steps of:
deriving a glutaminase from a culture of one or more microbes selected form the group consisting of *Bacillus amyloliquefaciens, Bacillus coagulans, Aspergilus niger, Rhizopus stolonifer, Saccharomyces cerevisiae, Saccharomyces rouxii, Candida utilis*, and *Candida Antarctica*; and reacting glutamine and an ethylamine with the derived glutaminase under conditions suitable to synthesize the theanine, wherein (i) the microbes are cultured so that the culture supernatant of the microbes has a specific activity of not less than 10 mU/mg, (ii) a ratio of the theanine synthesized from the glutaminase as a main product to glutamic acid synthesized from the glutaminase as a by-product is larger than 5, (iii) the method has a pH in a range of 9 to 12, (iv) the mol conversion ratio of L-glutamine to theanine is at least 70%, and (v) the mol conversion ratio of L-glutamine to glutamic acid is not more than 6%.

2. The method according to claim 1, wherein the glutaminase is fixed to a carrier.

3. The method according to claim 1, wherein the mol conversion ratio from L-glutamine to theanine is from 70% to 78%.

4. The method according to claim 1, wherein one or more microbes selected from the group consisting of *Bacillus amyloliquefaciens, Bacillus coagulans, Aspergilus niger, Saccharomyces cerevisiae, Saccharomyces rouxii, Candida utilis* and *Candida Antarctica*.

5. The method according to claim 1, wherein one or more microbes selected from the group consisting of *Aspergilus niger, Rhizopus stolonifer*.

6. The method according to claim 1, wherein one or more microbes selected from the group consisting of *Saccharomyces cerevisiae, Saccharomyces rouxii, Candida utilis* and *Candida antarctica*.

* * * * *